(12) United States Patent
Ohshima et al.

(10) Patent No.: US 7,037,298 B2
(45) Date of Patent: May 2, 2006

(54) DISPOSABLE ABSORBENT ARTICLE HAVING A RAISED CIRCUMFERENTIAL BANK

(75) Inventors: Kenji Ohshima, Kobe Hyogo (JP); Yuka Momotani, Nishinomiya Hyogo (JP); Kieko Imai, Mishima-gun Osaka (JP)

(73) Assignee: The Procter & Gamble Company, Cincinnati, OH (US)

( * ) Notice: Subject to any disclaimer, the term of this patent is extended or adjusted under 35 U.S.C. 154(b) by 471 days.

(21) Appl. No.: 10/302,601

(22) Filed: Nov. 22, 2002

(65) Prior Publication Data

US 2003/0120233 A1     Jun. 26, 2003

Related U.S. Application Data

(60) Provisional application No. 60/342,732, filed on Dec. 20, 2001.

(51) Int. Cl.
    *A61F 13/15*     (2006.01)

(52) U.S. Cl. .................. 604/385.101; 604/385.01
(58) Field of Classification Search ........... 604/385.01, 604/385.101, 385.12, 385.19, 385.28
See application file for complete search history.

(56) References Cited

U.S. PATENT DOCUMENTS

| | | |
|---|---|---|
| 4,988,345 A | 1/1991 | Reising |
| 5,211,641 A | 5/1993 | Roos et al. |
| 5,447,506 A | 9/1995 | Lindquist |
| 5,578,025 A | 11/1996 | May |
| 5,599,337 A | 2/1997 | McCoy |
| 5,624,423 A * | 4/1997 | Anjur et al. ........... 604/385.21 |
| 6,241,714 B1 * | 6/2001 | Raidel et al. ........... 604/378 |

(Continued)

FOREIGN PATENT DOCUMENTS

GB     2 233 235 A     1/1991

(Continued)

*Primary Examiner*—Tatyana Zalukaeva
*Assistant Examiner*—C. Lynne Anderson
(74) *Attorney, Agent, or Firm*—Kevin C. Johnson; Ken K. Patel; Steven W. Miller

(57) ABSTRACT

The invention is directed to an improvement of performance for disposable absorbent articles to prevent a leakage of body discharges. A disposable absorbent article comprising: an absorbent body having an average width of from about 5 mm to about 30 mm. The first resilient material is disposed between the body facing surface and the garment facing surface of the absorbent article; and a first resilient material disposed between the body facing surface and the absorbent body in a circumferential manner such that at least a part of the body facing surface of the absorbent article forms a raised circumferential bank in the central region and a concave portion surrounded by the raised circumferential bank. The first resilient material is selected from the group consisting of a polymeric foam material, a fibrous material, an elastic material, a formed film material, an absorbent gelling material, and a mixture thereof. In another aspect of the invention, a disposable absorbent article has the body facing surface having a shape which forms a raised circumferential bank in the central region and a concave portion surrounded by the raised circumferential bank. The raised circumferential bank has an inside wall and an outside wall. The outside wall of the raised circumferential bank has an average slope angle of from about 5 degrees to about 85 degrees or from about 95 degrees to about 175 degrees.

13 Claims, 4 Drawing Sheets

U.S. PATENT DOCUMENTS 6,300,538 B1    10/2001  Lindquist
6,402,728 B1 *   6/2002  Otsubo ................. 604/385.19
6,716,204 B1 *   4/2004  D'Acchioli et al. ... 604/385.19
6,764,477 B1 *   7/2004  Chen et al. ............ 604/385.14

FOREIGN PATENT DOCUMENTS

| | | |
|---|---|---|
| JP | 05086320 U | 11/1993 |
| JP | 0819857 A | 7/1996 |
| JP | 10118118 A | 5/1998 |
| JP | 11113950 A | 4/1999 |
| JP | 2001017467 A | 1/2001 |
| WO | WO 95/31163 A1 | 11/1995 |
| WO | WO 96/20679 A2 | 7/1996 |
| WO | WO 97/09016 A1 | 3/1997 |
| WO | WO 98/19644 A1 | 5/1998 |

* cited by examiner

DISPOSABLE ABSORBENT ARTICLE HAVING A RAISED CIRCUMFERENTIAL BANK

CROSS REFERENCE TO RELATED APPLICATION

This application claims the benefit of U.S. Provisional Application No. 60/342,732, filed on Dec. 20, 2001.

FIELD OF THE INVENTION

The present invention relates to disposable absorbent articles. More particularly, the present invention relates to a disposable absorbent article which has a raised circumferential bank in the central region of the article.

BACKGROUND

Disposable absorbent articles such as sanitary napkins are devices that are typically worn in the crotch region of an undergarment. Sanitary napkins, for example, are designed to absorb and retain body fluids or discharges (e.g., menses) from the body of women and to prevent body and clothing soiling. More specifically, sanitary napkins are worn by women in a pair of panties that is normally positioned between the wearer's legs, adjacent to the perineum area. A wide variety of shapes and dimensions of sanitary napkins is currently used by women for the collection of body fluids.

It is desirable that sanitary napkins maintain contact with and conform as closely as possible to the wearer's body. Such a body-conforming capability increases the effectiveness of sanitary napkins by reducing the possibility that body fluids will travel around the perimeter of sanitary napkins and leak.

There have been a number of recent efforts in sanitary napkins and other disposable absorbent articles to prevent a leakage of body fluids from the products. For example, U.S. Pat. No. 5,312,386 issued to Correa et al. on May 17, 1994, discloses a disposable sanitary pad (or napkin) which has longitudinal compression lines formed on the body facing surface of the pad. This patent teaches that such compression lines allow the body facing surface of the pad to be brought closer to the point of discharge thereby improving a leakage problem from the longitudinal edges of the pad. Similarly, the Japanese Patent Laid-open (Kokai) Publication H10-99372 published on Apr. 21, 1998 discloses a sanitary napkin having longitudinal compressed grooves formed on both the body facing surface and the garment facing surface of the sanitary napkin. This publication states that this configuration allows the sanitary napkin to bend along the compressive grooves thereby improving a leakage problem.

However, in conventional sanitary napkins and pads including the above described ones, the central area which are in between the longitudinal compression lines or grooves normally rises (or tends to have an increased thickness) compared with the longitudinal compression lines or grooves, as a result of compression for the formation of the compression lines or grooves. This configuration tends to move the body fluids discharged on the body facing surface (i.e., a topsheet) away from the central area before they are acquired by the under layer(s) of the central area, and thus causing a leakage problem from the side edges and/or the end edges of sanitary napkins and pads.

Thus, there is a need for a disposable absorbent article that can provide an improved performance for preventing a leakage of body discharges.

SUMMARY

The present invention is directed to a disposable absorbent article comprising: an absorbent body disposed between the body facing surface and the garment facing surface of the absorbent article; and a first resilient material having an average width of from about 5 mm to about 30 mm. The first resilient material is disposed between the body facing surface and the absorbent body in a circumferential manner such that at least a part of the body facing surface of the absorbent article forms a raised circumferential bank in the central region and a concave portion surrounded by the raised circumferential bank. The first resilient material is selected from the group consisting of a polymeric foam material, a fibrous material, an elastic material, a formed film material, an absorbent gelling material, and a mixture thereof.

In another aspect of the invention, a disposable absorbent article has the body facing surface having a shape which forms a raised circumferential bank in the central region and a concave portion surrounded by the raised circumferential bank. The raised circumferential bank has an inside wall and an outside wall. The outside wall of the raised circumferential bank has an average slope angle of from about 5 degrees to about 85 degrees or from about 95 degrees to about 175 degrees.

In an yet another aspect of the invention, a disposable absorbent article comprising: an absorbent body disposed between the body facing surface and the garment facing surface of the absorbent article; and a resilient material disposed between the body facing surface and the absorbent body such that at least a part of the body facing surface of the absorbent article forms a raised saddle bank in the rear region. The first resilient material is selected from the group consisting of a polymeric foam material, a fibrous material, an elastic material, a formed film material, an absorbent gelling material, and a mixture thereof.

The foregoing answers the need for a disposable absorbent article that can provide an improved performance for preventing a leakage of body discharges.

These and other features, aspects, and advantages of the present invention will become evident to those skilled in the art from reading of the present disclosure.

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings in which:

DETAILED DESCRIPTION

Figure 1:
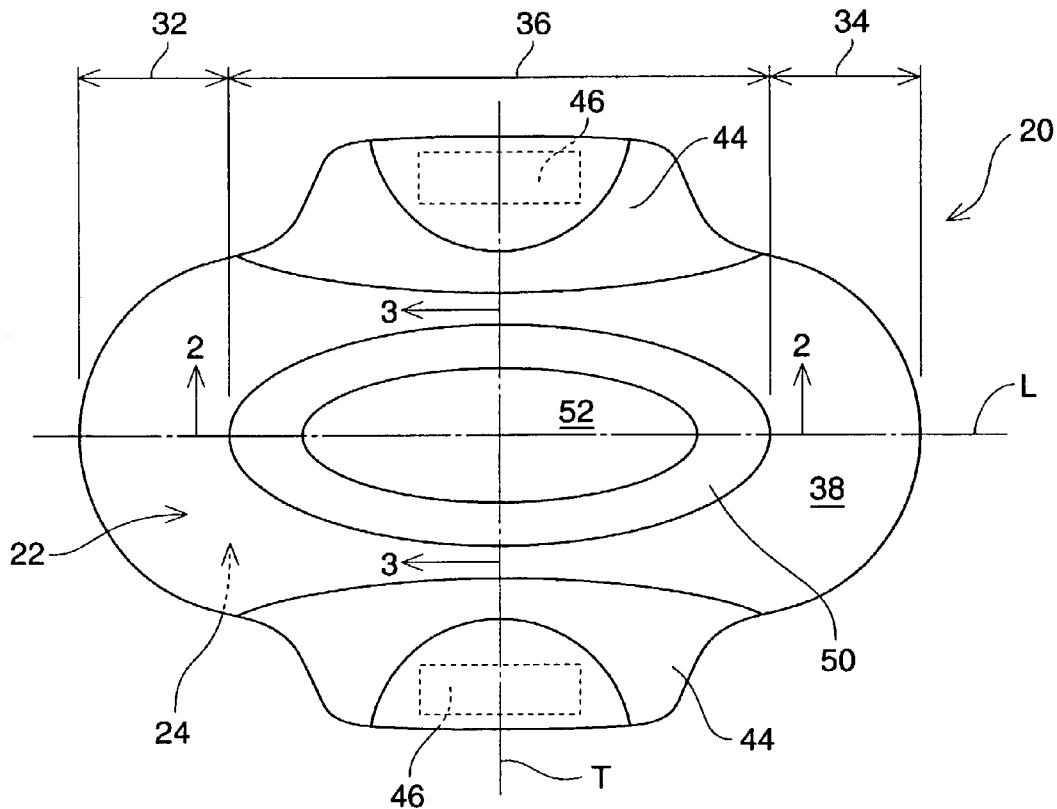
FIG. 1 is a top plan view of a sanitary napkin which is one preferred embodiment of the present invention.

All cited references are incorporated herein by reference in their entireties. Citation of any reference is not an admission regarding any determination as to its availability as prior art to the claimed invention.

Herein, "comprise" and "include" mean that other elements and/or other steps which do not affect the end result can be added. Each of these terms encompasses the terms "consisting of" and "consisting essentially of".

Herein, "absorbent article" refers to articles which absorb and contain body exudates or discharges, such as body fluids. More specifically, the term refers to articles which are placed against or in proximity to the body of the wearer to absorb and contain the various exudates discharged from the body. Herein, "absorbent article" is intended to include sanitary napkins, pantiliners, diapers, and incontinence pads (and other articles worn in the crotch region of a garment).

Herein, "disposable" refers to articles which are intended to be discarded after a single use and preferably recycled, composted, or otherwise disposed of in an environmentally compatible manner. (That is, they are not intended to be laundered or otherwise restored or reused as an absorbent article.)

Herein, "sanitary napkin" refers to articles which are worn by females adjacent to the pudendal region which are intended to absorb and contain the various exudates which are discharged from the body (e.g., blood, menses, and urine). Although the present invention is shown in the drawings as a sanitary napkin that is intended to replace conventional sanitary napkins, it should be understood that the present invention is not limited to the particular types or configurations of absorbent articles shown in the drawings.

Herein, "body facing surface" refers to surfaces of absorbent articles and/or their component members which face the body of the wearer, while the term "garment facing surface" refers to the opposite surfaces of the absorbent articles and/or their component members that face away from the wearer when the absorbent articles are worn. Absorbent articles and components thereof, including the topsheet, backsheet, absorbent body, and any individual layers of their components, have a body facing surface and a garment facing surface.

FIG. 1 is a top plan view of a sanitary napkin 20 (i.e., a disposable absorbent article) which is one preferred embodiment of the present invention. Referring to FIG. 1, the sanitary napkin 20 has a body facing surface 22, a garment facing surface 24 opposed to the body facing surface 22, front and rear end regions 32, 34, and a central region 36 disposed between the front and rear end regions 32, 34. The sanitary napkin 20 is shown in FIG. 1 as viewed from the body facing surface 22. The sanitary napkin 20 includes a resilient material 54 (not shown in FIG. 1 but FIGS. 2 and 3) disposed between the body facing surface 22 and the absorbent body 42 in a circumferential manner such that at least a part of the body facing surface 22 of the sanitary napkin 20 forms a raised circumferential bank 50 in the central region 36 and a concave portion 52 surrounded by the raised circumferential bank 50. In other words, the sanitary napkin 20 has, at a part of the body facing surface 22, the raised circumferential bank 50 in the central region 36 and the concave portion 52 surrounded by the raised circumferential bank 50.

The sanitary napkin 20 has two centerlines, a longitudinal centerline L and a transverse centerline T. Herein, "longitudinal" refers to a line, axis or direction in the plane of the sanitary napkin 20 that is generally aligned with (e.g., approximately parallel to) a vertical plane which bisects a standing wearer into left and right body halves when the sanitary napkin 20 is worn. Herein, "transverse" or "lateral", are interchangeable, and refer to a line, axis or direction which lies within the plane of the sanitary napkin 20 that is generally perpendicular to the longitudinal direction.

Figure 2:
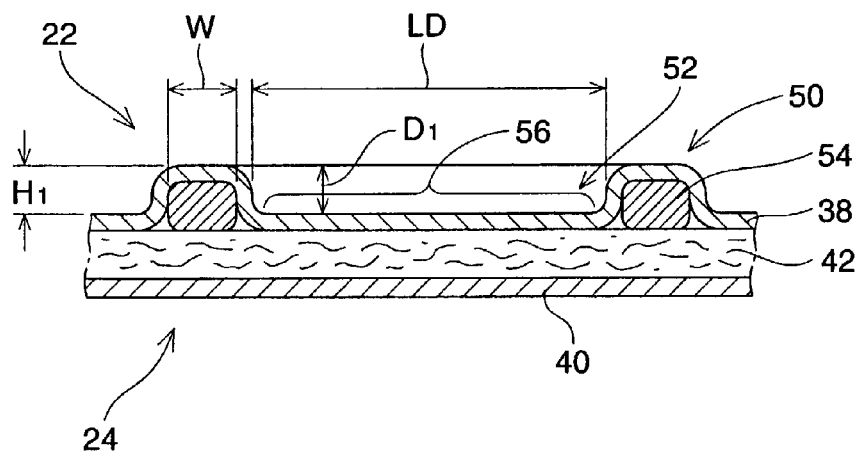
FIG. 2 is a cross-sectional view of the sanitary napkin shown in FIG. 1, taken along the line 2—2.
Figure 3:
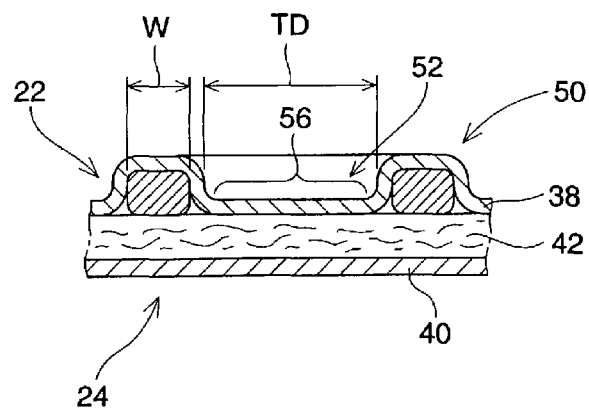
FIG. 3 is a cross-sectional view of the sanitary napkin shown in FIG. 1, taken along the line 3—3.

FIGS. 2 and 3 are cross-sectional views of the sanitary napkin 20 shown in FIG. 1, taken along the lines 2—2 and 3—3, respectively. The sanitary napkin 20 includes three primary components. These include a liquid pervious topsheet 38, a liquid impervious backsheet 40, and an absorbent body 42 disposed between the topsheet 38 and the backsheet 40. The topsheet 38 forms a part of (or the whole of) the body facing surface 22 of the sanitary napkin 20, and the backsheet 40 forms a part of (or the whole of) the garment facing surface 24 of the sanitary napkin 20. In other words, the absorbent body 42 is disposed between the body facing surface 22 and the garment facing surface 24 of the sanitary napkin 20.

As shown in FIGS. 2 and 3, the resilient material 54 has a width W in a direction which is parallel to the plane defined by the longitudinal centerline L and the transverse centerline T. The width W of the resilient material 54 may change depending on points or positions on the resilient material 54. (I.e., the resilient material 54 does not need to have a constant width W.) However, the width W of the resilient material 54 is preferably within a limited deviation. In preferred embodiments, the resilient material 54 has an average width from about 5 mm to about 30 mm, more preferably from about 8 mm to about 20 mm, and yet more preferably from about 8 mm to about 15 mm. By keeping the average width of the resilient material 54 within the range of 5–30 mm, the sanitary napkin 20 can provide an effective leakage prevention while providing a comfortable feel to the wearer. For example, if the average width of the resilient material 54 would be greater than about 30 mm, the sanitary napkin 20 would become bulky thereby causing an uncomfortable feel to the wearer. On the other hand, if the average width of the resilient material 54 would be less than about 5 mm, the sanitary napkin 20 could not provide an enough performance for preventing a leakage of body discharges.

The raised circumferential bank 50 can take any circumferential shape in its top plan view as long as it forms a circumferential bank. Herein, "circumferential" refers to a raised element (i.e., a raised bank) that forms a closed loop in its top plan view. Herein, "raised" refers to an element that is higher than its adjacently surrounding element(s) at every portions of the element. Preferred shapes for the raised circumferential bank 50 include an oval (as shown in FIG. 1) and a circle, although the any other shapes can be taken, for example, a triangle, a rectangle including a square, a pentagon, a hexagon, or the like.

The concave portion 52 can take any cross-sectional bottom shape. Preferably, the concave portion 52 has a flat cross-sectional bottom shape as shown in FIGS. 2 and 3, i.e., the concave portion 52 has its bottom 56 formed substantially flat. In an alternative preferred embodiment, the bottom 56 of the concave portion 52 takes a curved configuration such as a convexly curved cross-sectional bottom shape (shown in FIGS.). Further, the bottom 56 of the concave portion 52 can take a concavely curved cross-sectional bottom shape (shown in FIGS.). The flat cross-sectional bottom shape is particularly preferred than the curved configuration (in particular than the convexly curved cross-sectional bottom shape) since the raised circumferential bank 50 can effectively prevent body fluids which tend to flow on the body facing surface 22 of the topsheet 38 from flowing over the bank 50.

Preferably, the raised circumferential bank 50 should be appropriately sized and positioned in the central region 36 of the sanitary napkin 20 so that the concave portion 52 covers at least the labia minora of the wearer when the sanitary napkin 20 is worn. Such a configuration allows the sanitary napkin 20 to receive body fluids closely from the fluid source and within the concave portion 52 thereby effectively securing an effective leakage prevention by the raised circumferential bank 50.

The internal diameters of the raised circumferential bank 50 should be within an appropriate range for an effective leakage prevention. As shown in FIGS. 2 and 3, the concave portion 52 of the sanitary napkin 20 has a longitudinal internal diameter LD and a traverse internal diameter TD. Preferably, the longitudinal internal diameter LD is from about 40 mm to about 200 mm, and more preferably from about 60 mm to about 140 mm. The traverse internal diameter TD is preferably from about 20 mm to about 70 mm, and more preferably from about 30 mm to about 60 mm.

Figure 4:
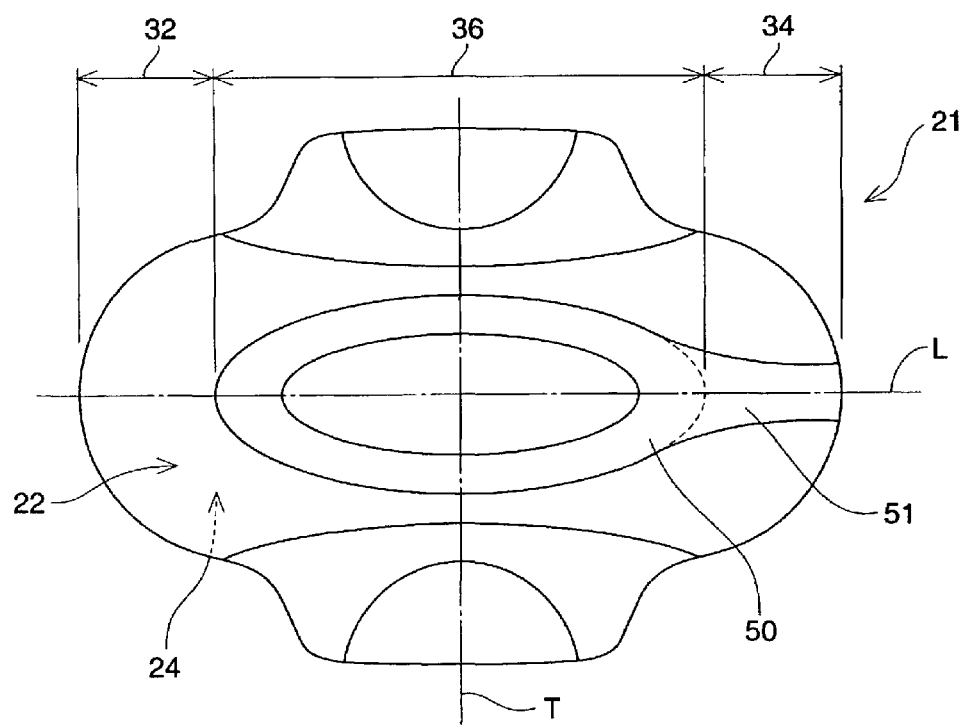
FIG. 4 is a top plan view of a sanitary napkin which is another preferred embodiment of the present invention.

FIG. 4 is a top plan view of a sanitary napkin 21 which is another preferred embodiment of the present invention. Referring to FIG. 4, the sanitary napkin 21 has a body facing surface 22, a garment facing surface 24 opposed to the body facing surface 22, front and rear end regions 32, 34, and a central region 36 disposed between the front and rear end regions 32, 34. Compared with the sanitary napkin 20 shown in FIG. 1, the body facing surface 22 of the sanitary napkin 21 additionally forms a raised saddle bank 51 in the rear region 34. The sanitary napkin 21 comprises an absorbent body (not shown in FIG. 4) disposed between the body facing surface 22 and the garment facing surface of the sanitary napkin 21; and a resilient material (not shown in FIG. 4) disposed between the body facing surface 22 and the absorbent body such that at least a part of the body facing surface of the absorbent article forms the raised saddle bank 51 in the rear region. The raised saddle bank 51 is preferably formed as an extended portion of the raised circumferential bank 50, which is disposed along the longitudinal center line L as shown in FIG. 4. Such an extended portion can be formed by disposing an additional (or second) resilient material (not shown in FIGS.) between the body facing surface 22 of the napkin 21 and the absorbent body 42 such that at least a part of the body facing surface 22 further forms the raised saddle bank 51 in the rear end region 34 of the sanitary napkin 21. Alternatively, if desired, the raised saddle bank 51 may be solely formed (i.e., without the raised circumferential bank 50).

The raised saddle bank 51 is sized and shaped such that it can closely fit the wearer's perineum region when the sanitary napkin 21 is worn, thereby effectively preventing a leakage of body fluids from the rear end region 34. The other portions of the sanitary napkin 21 of FIG. 4 are preferably formed similarly to those of the sanitary napkin 20 shown in FIG. 1.

The raised circumferential bank 50 of the present invention has a recovery rate of at least about 50%. Preferably, the raised circumferential bank 50 has a recovery rate of at least about 60%, and more preferably at least about 85%. In addition, the raised circumferential bank 50 of the invention has a compressive depth of at least about 1 mm under a pressure of 50 g/cm$^2$. Preferably, the raised circumferential bank 50 has a compressive depth of at least about 2 mm, and more preferably at least about 3 mm, under a pressure of 50 g/cm$^2$. The recovery rate should be within an appropriate range since if it is not within the range (i.e., below 50%), the raised circumferential bank 50 can not maintain a necessary height, and thus it can not fully prevent body fluids from flowing over the bank 50 when the sanitary napkin 20 is worn and pushed by the wearer's body. The compressive depth under a pressure of 50 g/cm$^2$ should also be within an appropriate range since if it is not within the range (i.e., below 1 mm), the raised circumferential bank 50 becomes hard thereby causing skin irritations and uncomfortable feel to the wearer. Methods for measuring these properties will be described in the "Test Methods" section.

In a preferred embodiment, the raised saddle bank 51 shown in FIG. 4 also has a recovery rate of at least about 50%. Preferably, the raised saddle bank 51 has a recovery rate of at least about 60%, and more preferably at least about 85%. In addition, the raised saddle bank 51 has a compressive depth of at least about 1 mm under a pressure of 50 g/cm$^2$. Preferably, the raised saddle bank 51 has a compressive depth of at least about 2 mm, and more preferably at least about 3 mm, under a pressure of 50 g/cm . The recovery rate should be within an appropriate range since if it is not within the range (i.e., below 50%), the raised saddle bank 51 can not maintain necessary height, and thus it can not fully prevent body fluids from flowing over the bank 51 when the sanitary napkin 21 is worn and pressed by the wearer's body. The compressive depth under a pressure of 50 g/cm$^2$ should also be within an appropriate range since if it is not within the range (i.e., below 1 mm), the raised saddle bank 51 becomes hard thereby causing skin irritations and uncomfortable feel to the wearer.

The raised circumferential bank 50 (and the raised saddle bank 51 if desired) can be formed by a single member or a combination of a plurality of component members which is (or are) disposed on the absorbent body 42. When the raised circumferential bank 50 (and the raised saddle bank 51) is formed by a single resilient member, a part of such a material (i.e., the body facing surface of the material) works as (or forms) a liquid pervious topsheet 38. Alternatively, the raised circumferential bank 50 (and the raised saddle bank 51) is formed by a combination of a plurality of component members as shown in the embodiment of FIGS. 1–3. Specifically, the raised circumferential bank 50 includes (or is formed by) a part of the topsheet 38 and a resilient material 54 which is disposed in a circumferential manner on the body facing surface of the absorbent body 42. Preferably, the resilient material 54 is disposed between the garment facing surface of the topsheet 38 and the body facing surface of the absorbent body 42 as shown in FIGS. 2 and 3. However, the resilient material 54 can be positioned between any of the components between the body facing surface 22 and the garment facing surface 24 of the sanitary napkin 20.

In a preferred embodiment, the resilient material 54 includes a single piece of a resilient material which is disposed in a circumferential manner. However, if desired, the resilient material 54 can include a plurality of pieces of a resilient material(s) which are disposed in a circumferential manner, whereby the raised circumferential bank 50 is divided into a plurality of raised portions (not shown in FIGS.). Such pieces of the resilient material 54 can be disposed on the body facing surface of the absorbent body 42 with either an overlapped manner or a non-overlapped manner. Preferred materials for the resilient material 54 include a moldable material which is selected from the group consisting of a polymeric foam material, a fibrous material, an elastic material, a formed film material, an absorbent gelling material, and a mixture thereof.

The resilient material 54 can be in any suitable form, including, but not limited to masses or wads of material, single unfolded sheets, folded sheets, strips of material, loose or bonded fibers (i.e., fibrous materials), and multiple layers or laminates of material. The resilient material 54 can be a homogeneous single material, a homogeneous mixture of different materials, or a non-homogeneous combination of different materials (e.g., a layered construction). The resilient material 54 can be wrapped in a web of nonwoven or tissue material.

Preferred resilient materials for the raised circumferential bank 50 and/or the raised saddle bank 51 include a resilient material which is selected from the group consisting of a fibrous material, a polymeric foam material, an elastic material, a formed film material, an absorbent gelling material, and a mixture thereof.

The resilient material may have an absorbent capacity. Alternatively, the resilient material may have substantially no absorbent capacity. If the resilient material has an absorbent capacity, it preferably maintains at least some rigidity when it is wet.

Preferred fibrous materials for the resilient material 54 include synthetic fibers and/or natural fibers such as highloft polyesters, rayons, and other polyolefin materials and blends thereof. If desired, the resilient material 54 can be made from the same materials as those used in the absorbent body (or core) 42.

In one preferred embodiment, the resilient material 54 include capillary channel fibers or chemically modified natural fibers, such as cross-linked cellulose fibers. Suitable cross-linked cellulose fibers are described in U.S. Pat. No. 4,888,093, issued on Dec. 19, 1989 to Cook et al.; U.S. Pat. No. 4,822,543, issued on Apr. 18, 1989 to Dean, et al.; U.S. Pat. No. 4,889,559, issued on Dec. 26, 1989 to Schoggen, et al.; U.S. Pat. No. 4,898,642, issued on Feb. 6, 1990 to Moore, et al.; and U.S. Pat. No. 4,935,022 issued on Jun. 19, 1990 to Lash et al.

In an alternative preferred embodiment, the resilient material 54 includes a bi-component fibrous material including bi-component fibers having a core of polypropylene which is coated with a sheath of polyethylene. The outside of the bi-component fibers have a lower melting temperature than the inside. Such a material is preferred because the fibers can be heat bonded to each other by melting the outside of the fibers while the inside of the fibers maintain their fibrous integrity instead of melting into an amorphous mass. Suitable bi-component fibers are commercially available from of Chisso Corporation, Tokyo, Japan, under Code No. ESC-UB (or ESC-SB or ETC).

Preferred polymeric foam materials for the resilient material 54 include absorbent foams such as a polyurethane foam and an HIPE foam which is developed from high internal phase emulsions (HIPE's) or other combinations of such material known in the art as functional absorbent materials or FAM foams. A preferred polyurethane foam material is available from Kurabo Industries, Ltd., Osaka, Japan, under Code No. Kurarafoam281. Preferred HIPE foam materials are disclosed in U.S. Pat. No. 5,260,345, issued to DesMarais, et al. on Nov. 9, 1993; U.S. Pat. No. 5,387,207, issued to Dyer, et al. on Feb. 7, 1995; U.S. Pat. No. 5,563,179, issued to Stone, et al. on Oct. 8, 1996; and U.S. Pat. No. 5,899,893, issued to Dyer, et al. on May 4, 1999.

Preferred elastic materials for the resilient material 54 include natural rubbers, synthetic rubbers, and a bundled or combined materials of such materials or other materials generally known in the art as an elastic material. A preferred natural rubber material is available from Fulflex Inc, Rhode Island, U.S.A., under Code No. 941W1. A preferred synthetic rubber material is available from Toray-Dupont, Tokyo, Japan, under Code No. LYCRA.

Preferred formed film materials for the resilient material 54 include vacuum formed three-dimensional film and other films formed by other methods. Preferred vacuum formed three-dimensional film materials are available from Tredegar Corporation, Virginia, U.S.A., under Code No. X-15507 and X-15895.

Preferred absorbent gelling materials for the resilient material 54 include a polyacrylate sodium salt, other absorbent gelling materials generally known in the art, and a blend of such materials. The absorbent gelling materials are preferably mixed with a liquid absorbent material such as a comminuted wood pulp which is generally referred to as airfelt, or other liquid absorbent material(s) known in the art. A preferred absorbent gelling material is a polyacrylate sodium salt which is available from Nippon Shokubai Co. Ltd., Osaka, Japan, under Code No. L-74.

Figure 5:
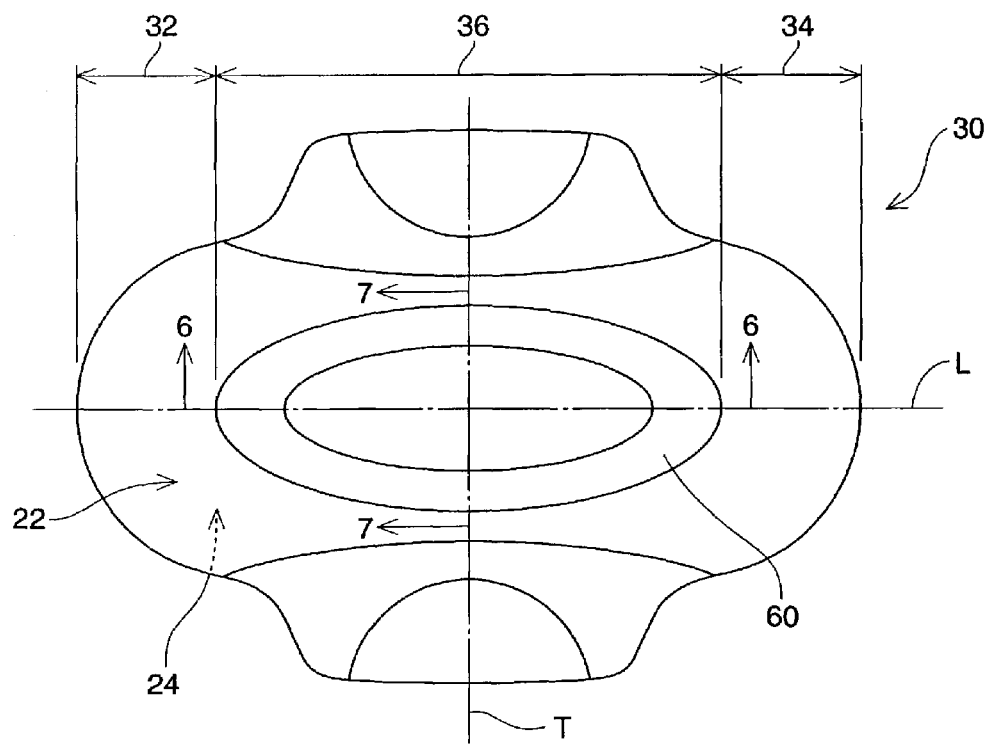
FIG. 5 is a top plan view of a sanitary napkin which is another preferred embodiment of the present invention.

FIG. 5 is a top plan view of a sanitary napkin 30 which is another preferred embodiment of the present invention. Referring to FIG. 5, the sanitary napkin 30 has a body facing surface 22, a garment facing surface 24 opposed to the body facing surface 22, front and rear end regions 32, 34, and a central region 36 disposed between the front and rear end regions 32, 34. The sanitary napkin 30 is shown in FIG. 5 as viewed from the body facing surface 22. The sanitary napkin 20 has two centerlines, a longitudinal centerline L and a transverse centerline T.

Figure 6:
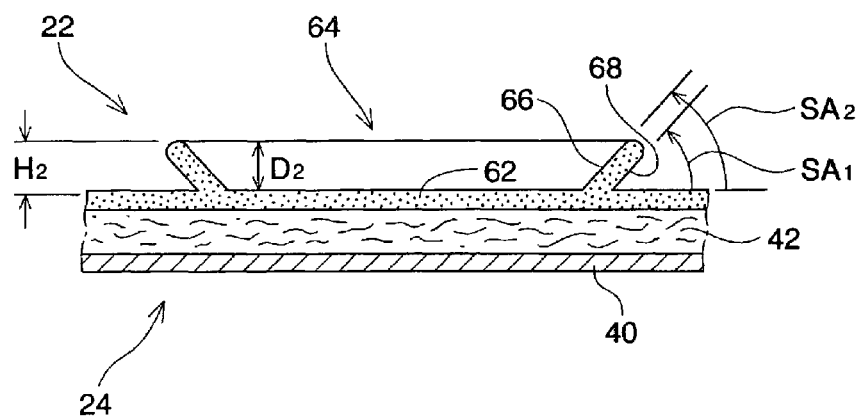
FIG. 6 is a cross-sectional view of the sanitary napkin shown in FIG. 5, taken along the line 6—6.
Figure 7:
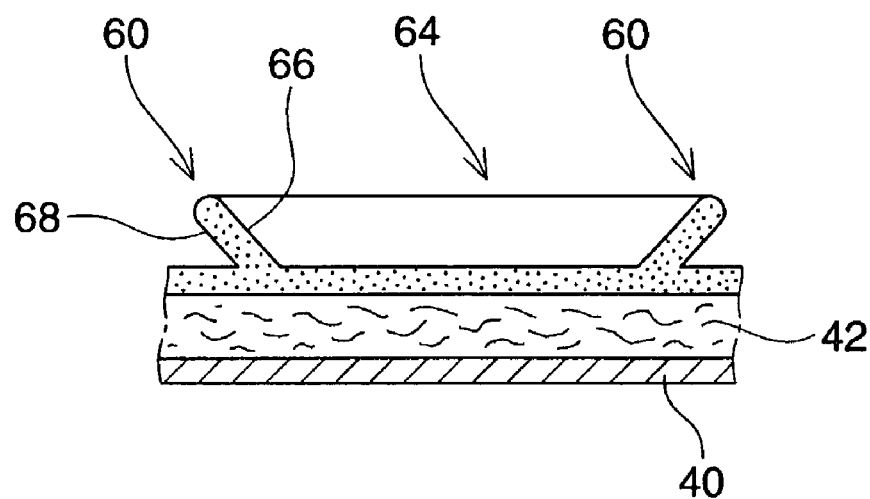
FIG. 7 is a cross-sectional view of the sanitary napkin shown in FIG. 5, taken along the line 7—7.

FIGS. 6 and 7 are cross-sectional views of the sanitary napkin 30 shown in FIG. 5, taken along the lines 6—6 and 7—7, respectively. The sanitary napkin 30 includes three primary components. These include a liquid pervious body facing sheet 62, a liquid impervious backsheet 40, and an absorbent body 42 disposed between the body facing sheet 62 and the backsheet 40. The body facing sheet 62 forms a part of (or the whole of) the body facing surface 22 of the sanitary napkin 30, and the backsheet 40 forms a part of (or the whole of) the garment facing surface 24 of the sanitary napkin 30.

As shown in FIGS. 6 and 7, the body facing surface of the sanitary napkin 30 has a shape which forms a raised circumferential bank 60 in the central region 36 and a concave portion 64 surrounded by the raised circumferential bank 60. The raised circumferential bank 60 has an inside wall 66 and an outside wall 68. As shown in FIGS. 6 and 7, each of the inside wall 66 and the outside wall 68 has a slope having an average slope angle SA1 or SA2. The average slope angles SA1 and SA2 are measured from the body facing surface 22 of the outside region of the raised circumferential bank 60 to the outside wall 68 and the inside wall 66, respectively, as shown in FIG. 6. The average slope angle is defined as the average angle value of the respective circumferential slope of the wall.

In the sanitary napkin 30 shown in FIG. 6, the outside wall 68 of the raised circumferential bank 60 has an average slope angle SA1 of from about 5 degrees to about 85 degrees, and more preferably from about 60 degrees to about 85 degrees. In addition, the inside wall 66 of the raised circumferential bank 60 preferably has an average slope angle SA2 of from about 5 degrees to about 85 degrees, and more preferably from about 60 degrees to about 85 degrees.

In an alternative preferred embodiment (not shown in FIGS.), the outside wall 68 of the raised circumferential bank 60 has an average slope angle SA1 of from about 95 degrees to about 175 degrees, and more preferably from about 150 degrees to about 175 degrees. In addition, the inside wall 66 of the raised circumferential bank 60 preferably has an average slope angle SA2 of from about 95 degrees to about 175 degrees, and more preferably from about 150 degrees to about 175 degrees.

As shown in FIGS. 5-7, the raised circumferential bank 60 is preferably formed by a homogeneous single material. However, if desired, the raised circumferential bank 60 can be formed by a homogeneous mixture of different materials, or a non-homogeneous combination of different materials.

In a preferred embodiment, the body facing surface 22 of the sanitary napkin 30 additionally has a second concave portion (not shown in FIGS.) which is additionally formed on the outside region of the raised circumferential bank 60 to surround the raised circumferential bank 60 such that the raised circumferential bank 60 is disposed within the second concave portion. Alternatively (or additionally), the body facing surface 22 of the sanitary napkin 30 may further form a raised saddle bank (not shown in FIGS. 5–7) in the rear region 34 which is similar to the raised saddle bank 51 shown in FIG. 4.

As shown in FIGS. 2 and 3, the raised circumferential bank 50 has a height H1 which is measured from the body facing surface 22 of the front (or the rear) end region 32, as shown in FIG. 2. In a preferred embodiment, the raised circumferential bank 50 has a height H1 of at least about 1 mm, preferably between about 2 mm and about 10 mm, and more preferably between about 3 mm and about 5 mm. The concave portion 52 has a depth D1 which is measured from the top of the raised circumferential bank 50, as shown in FIG. 2. In a preferred embodiment, the raised circumferential bank 50 has a depth D1 of at least about 1 mm, preferably between about 2 mm and about 10 mm, and more preferably between about 3 mm and about 5 mm.

As shown in FIGS. 6 and 7, the raised circumferential bank 60 has a height H2 which is measured from the body facing surface 22 of the front (or the rear) end region 32, as shown in FIG. 6. In a preferred embodiment, the raised circumferential bank 60 has a height H2 of at least about 1 mm, preferably between about 2 mm and about 10 mm, and more preferably between about 3 mm and about 5 mm. The concave portion 54 has a depth D2 which is measured from the top of the raised circumferential bank 60, as shown in FIG. 6. In a preferred embodiment, the raised circumferential bank 60 has a depth D2 of at least about 1 mm, preferably between about 2 mm and about 10 mm, and more preferably between about 3 mm and about 5 mm.

The sanitary napkins 20, 21 and 30 can generally have any thickness including relatively thick, intermediate thickness, relatively thin, or even very thin (or "ultra thin"), except at the portion of the raised circumferential bank 50 (or 60) in the central region 36. An "ultra-thin" sanitary napkin as described in U.S. Pat. Nos. 4,950,264 and 5,009,653 issued to Osborn preferably has a caliper of less than about 3 mm. The embodiment of the sanitary napkins 20, 21 and 30 shown in the drawings is intended to be examples of an ultra-thin sanitary napkin. The sanitary napkins 20, 21 and 30 may also be relatively flexible, so that they are comfortable for the wearer. It should, however, be understood that the sanitary napkins 20, 21 and 30 shown are merely embodiments of the present invention which is not limited to absorbent articles of the type or having the specific configurations shown in the drawings.

In a preferred embodiment shown in FIGS. 1–3, an acquisition layer or a secondary topsheet (not shown in FIGS.) is additionally disposed above the resilient material 54 and/or the absorbent body 42 (and below the garment facing surface of the topsheet 38). The acquisition layer quickly transports discharged body fluids received by the topsheet 38 to other parts of the acquisition layer and the absorbent body 42, although it may temporarily hold such fluids until they can be absorbed by the absorbent body 42. The distribution function of the acquisition layer is of particular importance in order to more fully utilize the capacity of the absorbent body 42. Thus, while the acquisition layer may comprise a wide variety of absorbent materials, it preferably comprises a fibrous material that can rapidly transport fluid and not collapse upon being wetted so that the acquisition layer can effectively acquire and distribute second and successive fluids.

The acquisition layer can be made from any materials which have fluid transportation functions known in the art. The acquisition layer may, for example, be comprised of woven, nonwoven or tissue materials. The fibers or other components of these materials may be synthetic or natural, or partially synthetic and partially natural. Suitable synthetic fibers include polyester, polypropylene, polyethylene, nylon, viscous rayon, or cellulose acetate fibers. Suitable natural fibers include cotton, cellulose, or other natural fibers. The acquisition layer may also be at least partially comprised of cross-linked cellulose fibers. The acquisition layer, if it is a nonwoven, can be made by a number of different processes. These include, but are not limited to: air laid, wet laid, meltblown, spunbonded, carded, thermally bonded, air-through bonded, powder bonded, latex bonded, solvent bonded, spunlaced, and a combination. In one preferred embodiment, the acquisition layer is an air laid tissue material which is available from Concert GmbH, Falkenhagen, Germany under Code No. GH082. In another preferred embodiment, the acquisition layer is an air laid tissue material which is available from Buckeye Cellulose Co., Tenn., U.S.A. under Code No. FG613MHB.

In general, the absorbent body 42 is capable of receiving, absorbing or retaining body fluids discharged (e.g., menses, urine, and other body exudates). The absorbent body 42 is preferably compressible, conformable, and non-irritating to the wearer's skin. The absorbent body 42 may be manufactured in a wide variety of sizes and shapes (e.g., rectangular, oval, hourglass, "T" shaped, dog bone, asymmetric, etc.). The absorbent body 42 can be formed by a single layer material or a plurality of layered materials. The absorbent body may include any of a wide variety of liquid-absorbent materials commonly used in absorbent articles, such as comminuted wood pulp, which is generally referred to as airfelt. Examples of other suitable absorbent materials for use in the absorbent body include creped cellulose wadding; meltblown polymers including coform; chemically stiffened, modified or cross-linked cellulosic fibers; synthetic fibers such as crimped polyester fibers; peat moss; tissue including tissue wraps and tissue laminates; absorbent foams; absorbent sponges; absorbent gelling materials; or any equivalent material or combinations of materials, or mixtures of these. Herein, "chemically stiffened fibers" means any fibers which have been stiffened by chemical means to increase stiffness of the fibers under both dry and wet conditions. Such means include the addition of chemical stiffening agents which, for example, coat and/impregnate the fibers. Such means also include the stiffening of the fibers by altering the chemical structure of the fibers themselves, e.g., by cross-linking polymer chains. In one preferred embodiment, the component fibers are cellulosic fibers which are coated or impregnated with a chemical stiffening agent. Preferred agents for such a chemical stiffening agent include polycarboxylates such as a citric acid. The polycarboxylate stiffening agents and a process for making stiffened fibers from them are described in U.S. Pat. No. 5,190,563, issued to Herron et al. on Mar. 2, 1993.

In one preferred embodiment, the absorbent body is an air laid tissue material which is available from Concert GmbH, Falkenhagen, Germany under Code No. GH150. In another preferred embodiment, the absorbent body is an air laid tissue material which is available from Buckeye Cellulose Co., Tenn., U.S.A. under Code No. Foley NMC.

The backsheet 40 is impervious to body fluids and is preferably manufactured from a thin plastic film, although other flexible liquid impervious materials may also be used. Herein, "flexible" refers to materials which are compliant and will readily conform to the general shape and contours of the human body. The backsheet 40 prevents the body fluids absorbed and contained in the absorbent body 42 from wetting articles which contact the absorbent article such as bedsheets, pants, pajamas and undergarments. The backsheet 40 may thus include a woven or nonwoven material, polymeric films such as thermoplastic films of polyethylene or polypropylene, or composite materials such as a film-coated nonwoven material. A suitable backsheet material is a polyethylene film having a thickness of from about 0.012 mm (0.5 mil) to about 0.051 mm (2.0 mils). A preferred backsheet material is a polyethylene film which is available from Clopay Co., Ohio, U.S.A., under Code No. DH-215. The backsheet 40 may be embossed and/or matte finished to provide a more clothlike appearance. Further, the backsheet 40 may permit vapors to escape from the absorbent body (i.e., the backsheet is breathable) while still preventing body fluids from passing through the backsheet. A preferred microporous polyethylene film which is available from Mitsubishi Chemical Corporation, Tokyo, Japan, under Code No. NPP2. The size of the backsheet is dictated by the size of the absorbent body and the exact absorbent article design selected.

A suitable breathable backsheet material is a laminate of an apertured film such as that described in U.S. Pat. No. 3,929,135 issued to Thompson which is inverted so that the smaller openings of the tapered capillaries face the absorbent body 42 which is adhesively laminated to a microporous film such as that described in U.S. Pat. No. 4,777,073 issued to Sheth on Oct. 11, 1988.

The topsheet 38 is preferably compliant, soft feeling, and non-irritating to the wearer's skin. Further, the topsheet 38 is liquid pervious, permitting liquids (e.g., menses and/or urine) to readily penetrate through its thickness. A suitable topsheet may be manufactured from a wide range of materials such as woven and nonwoven materials (e.g., a non-woven web of fibers); polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers) or from a combination of natural and synthetic fibers. When the topsheet 38 includes a nonwoven web, the web may be manufactured by a wide number of known techniques. For example, the web may be spunbonded, carded, wet-laid, melt-blown, hydroentangled, combinations of the above, or the like.

A particularly suitable topsheet for use in the sanitary napkins disclosed includes an apertured formed film. Apertured formed films are preferred for the topsheet 38 because they are pervious to body exudates and, if properly apertured, have a reduced tendency to allow liquids to pass back through and rewet the wearer's skin. Thus, the body facing surface of the formed film (i.e., the body facing surface 22 of the sanitary napkin) remains dry, thereby reducing body soiling and creating a more comfortable feel for the wearer.

Preferably, the body facing surface 22 of the sanitary napkin is hydrophilic so that liquids will be transferred through the topsheet 38 more readily. If the topsheet 22 is made of a hydrophobic material, at least the upper surface (i.e., the body facing surface 22) of the topsheet 38 is treated to be hydrophilic so that liquids will transfer through the topsheet 38 more rapidly. This diminishes the likelihood that menstrual fluid will flow off the topsheet rather than flowing into and being absorbed by the absorbent body. The body facing surface of the topsheet 38 can be made hydrophilic by treating it with a surfactant. A preferred topsheet material is an apertured polyethylene film which is available from Tredegar, Virginia, U.S.A. under Code No. X-15507.

The absorbent body 42 is preferably joined with the topsheet 38, the backsheet 40, or both in any manner as is known by attachment means such as those well known in the art. The resilient material 54 is also preferably joined with the topsheet 38 and/or the absorbent body 42. Herein, "joined" encompasses configurations in which an element is directly secured to another element by affixing the element directly to the other element; configurations in which the element is indirectly secured to the other element by affixing the element to intermediate member(s) which in turn are affixed to the other element; and configurations in which one element is integral with another element, i.e., one element is essentially part of the other element. The backsheet 40 and/or the topsheet 38 may be joined to the absorbent body 42 or to each other by a uniform continuous layer of adhesive, a patterned layer of adhesive, or an array of separate lines, spirals, or spots of adhesive.

The portions of the topsheet 38 and backsheet 40 that extend beyond the edges of the absorbent body 42 are preferably also joined to each other. Preferably, these portions of the topsheet 38 and backsheet 40 are joined using adhesives over substantially the entire portions that extend beyond the edges of the absorbent body 42 and a crimp seal at the end edges of the sanitary napkin 20 where the topsheet 38 and backsheet 40 are densified by the application of pressure or heat and pressure.

The sanitary napkin 20 can include an optional pair of flaps 44 as shown in FIG. 1. The flaps 44 extend outward from at least the central region 36 of the sanitary napkin 20. The flaps 44 can be in any suitable configuration known in the art.

The garment facing surface 24 of the sanitary napkin 20 preferably includes fasteners for attaching the sanitary napkin 20 to the wearer's undergarment. Such fasteners include a central pad fastener (not shown in FIGS.) and a flap fastener. The central pad fastener is adapted to secure the sanitary napkin 20 to the crotch region of an undergarment. Any types of fasteners known in the art, such as adhesive fasteners and mechanical fasteners can be used. A preferred central pad fastener is a pressure-sensitive adhesive. In a preferred embodiment, the central pad fastener includes a pair of spaced apart longitudinally-oriented strips or zones (not shown in FIGS.) of adhesive that are centered about the longitudinal centerline L.

The garment facing surface of the flaps 44, adjacent the distal edges of the flaps 44, is preferably provided with a flap fastener 46. The flap fastener 46 is used to assist in maintaining the flaps 44 in position after they are wrapped around the edge of the crotch portion of the panty. A preferred flap fastener is a pressure-sensitive adhesive. The flaps 44 can be maintained in position by attaching the flaps 44 to the undergarment, or to the opposing flap.

The fasteners are not limited to adhesive attachment means. Any type of fastener used in the art can be used for such purpose. For example, the sanitary napkin 20 could be secured to the wearer's undergarment by mechanical fasteners, such as VELCRO.

The adhesive attachment means are respectively covered by removable release liners, i.e., a central pad release liner and a flap release liner. These release liners are provided to protect the adhesive attachment means of the fasteners before use. The pressure-sensitive adhesives should be covered with the release liners to keep the adhesives from sticking to extraneous surfaces prior to use.

TEST METHODS

This method describes a procedure that is used for determining a recovery rate and a compressive depth of a sample absorbent article against an externally applied compression. In general, this procedure involves a measurement of change of a resilient pressure which is generated when a sample absorbent article is pushed down by a predetermined probe at a probe contacting area of the sample member.

The test apparatus comprises a horizontal, smooth and rigid plate and a vertically movable bar which is positioned above the horizontal plate. The plate should be made of stainless steel or other rigid, non-corrosive metal. A preferred plate is a stainless steel plate.

A sample absorbent article having a raised bank on the body facing surface is placed and fixed on the horizontal plate such that the body facing surface of the sample article is exposed.

A probe which has a circular flat top of an area about 2 $cm^2$ is attached to the bar so that the top of the probe slightly contacts the raised bank of the sample article at an original pressure Po (0.5 $gf/cm^2$). The portion of the raised bank of the sample article where the top of the probe contacts is called as "probe contacting area". The probe is connected to a pressure sensor which measures, through the probe, the resilient pressure generated from the raised bank of the article at the probe contacting area.

The bar moves downwardly at a cross-head speed of about 20 μm/s until the resilient pressure Pm which is generated from the raised bank of the sample article at the probe contacting area becomes 50 $gf/cm^2$. Upon reaching to 50 $gf/cm^2$, the bar moves upwardly at the same speed (20 μm/s) until the probe is away from the probe contacting area. The resilient force which is measured by the sensor is continuously recorded by a recorder (e.g., a computer system). Preferably, this measurement is repeated at least 3 times on different sample articles which are assumed to produce similar data, and the average data are used in the below calculation.

A preferred test apparatus for the measurements is available from Kato Tech., Kyoto, Japan, under the Code No. "KES-FB3".

Figure 8:
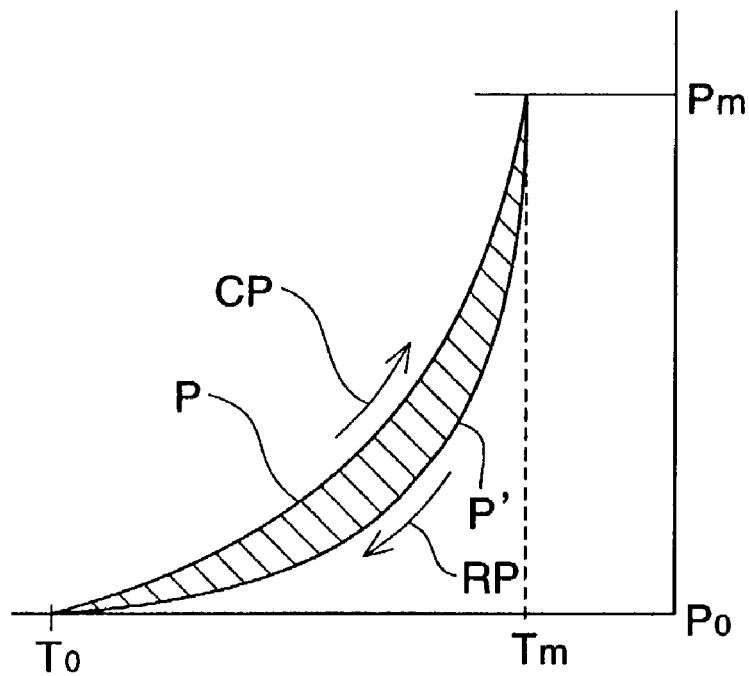
FIG. 8 is a graph showing one example of test data obtained from a sample article.

FIG. 8 is a graph which shows a simplified example of test data which is typically obtained by this test. In this graph, the horizontal axis shows a change of the compression depth, and the vertical axis shows a change of the resilient pressure. The resilient pressure P is shown in the compressing process CP, while the resilient pressure P' is shown in the returning process RP.

Based on the recorded data (preferably, the average data), a compression depth CD and a recovery rate RR are obtained by the following expressions:

$$CD = Tm - To \qquad (1)$$

$$RR = WC' / WC \times 100(\%) \qquad (2)$$

$$WC = \int_{Tm}^{To} P\,dx \qquad (3)$$

$$WC' = \int_{Tm}^{To} P'\,dx \qquad (4)$$

where

To: The original thickness (mm) of the sample article at the original pressure (Po=0.5 $gf/cm^2$);

Tm: The thickness (mm) of the sample article at the maximum pressure (Pm=50 $gf/cm^2$);

WC: The work ($gf \cdot cm/cm^2$) given by the resilient pressure P in the compressing process CP, which is obtained by the expression (3); and WC': Work ($gf \cdot cm/cm^2$) given by the resilient pressure P' in the returning process RP, which is obtained by the expression (4).

EXAMPLES

In the following Examples 1 and 2, each of the resilient materials which has an average width of 10 mm and an average thickness of 5 mm is disposed between the topsheet and the secondary topsheet. The resultant recovery rate (%) and compressive depth (mm) are shown in Table III.

TABLE 1

(Example 1)

| Component | Material | Code No. | Supplier |
|---|---|---|---|
| Topsheet | Apertured Polyethylene Film | X-15507 | Tredegar, Virginia, USA |
| Secondary Topsheet | Airlaid Tissue | GH082 | Concert GmbH, Falkenhagen, Germany |
| Absorbent Body | Airlaid Tissue | GH150 | Concert GmbH, Falkenhagen, Germany |
| Backsheet | Polyethylene Film (Microporous) | NPP2 | Mitsubishi Chemical Co., Tokyo, Japan |
| Resilient Material | Polyurethane Foam | Kurarafoam281 | Kurabo, Osaka, Japan |

TABLE II (Example 2)

| Component | Material | Code No. | Supplier |
|---|---|---|---|
| Topsheet | Apertured Polyethylene Film | X-15507 | Tredegar, Virginia, USA |
| Secondary Topsheet | Airlaid Tissue | FG613MHB | Buckeye Cellulose Co., Tenn., USA |
| Absorbent Body | Fluffed Pulp | Foley NMC | Buckeye Cellulose Co., Tenn., USA |

TABLE II-continued (Example 2)

| Component | Material | Code No. | Supplier |
|---|---|---|---|
| Backsheet | Polyethylene Film | DH-215 | Clopay Co., Ohio, USA |
| Resilient Material | Polyurethane Foam | Kurarafoam281 | Kurabo, Osaka, Japan |

TABLE III

| Example | Recovery Rate (%) | Compressive Depth (mm) |
|---|---|---|
| I | 63.5 | 2.6 |
| II | 90.5 | 4.7 |

It is understood that the examples and embodiments described herein are for illustrative purpose only and that various modifications or changes will be suggested to one skilled in the art without departing from the scope of the present invention.

What is claimed is:

1. A disposable absorbent article having a body facing surface, a garment facing surface opposed to the body facing surface, front and rear end regions, and a central region disposed between the front and rear end regions, the absorbent article comprising:
   an absorbent body disposed between the body facing surface and the garment facing surface;
   a first resilient material having an average width of from about 5 mm to about 30 mm, the first resilient material being disposed between the body facing surface and the absorbent body in a circumferential manner such that at least a part of the body facing surface of the absorbent article forms a raised circumferential bank in the central region and a concave portion surrounded by the raised circumferential bank;
   wherein the first resilient material is selected from the group consisting of a polymeric foam material, a fibrous material, an elastic material, formed film material, an absorbent gelling material, and a mixture thereof; and
   a second resilient material disposed between the body facing surface and the absorbent body such that at least a part of the body facing surface of the absorbent article forms a raised saddle bank in the rear region.

2. The absorbent article of claim 1, wherein the raised circumferential bank has a recovery rate of at least about 50%.

3. The absorbent article of claim 2, the raised circumferential bank has a compressive depth of at least about 1 mm under a pressure of 50 g/cm$^2$.

4. The absorbent article of claim 1 further comprising a liquid permeable topsheet forming at least a part of the body facing surface, and a liquid impermeable backsheet forming at least a part of the garment facing surface,
   wherein the absorbent body is disposed between the topsheet and the backsheet.

5. The absorbent article of claim 1, wherein the raised circumferential bank is sized and positioned in the central region so that the concave portion covers the labia minora of the wearer when the absorbent article is worn.

6. The absorbent article of claim 5, wherein the absorbent article is a sanitary napkin, and the concave portion has a longitudinal internal diameter of from about 40 mm to about 200 mm, and a traverse internal diameter of from about 20 mm to about 70 mm.

7. A disposable absorbent article having a body facing surface, a garment facing surface opposed to the body facing surface, front and rear end regions, and a central region disposed between the front and rear end regions, the absorbent article comprising an absorbent body disposed between the body facing surface and the garment facing surface;
   the body facing surface of the absorbent article having a shape which forms a raised circumferential bank in the central region and a concave portion surrounded by the raised circumferential bank, the raised circumferential bank having an inside wall and an outside wall;
   wherein the outside wall of the raised circumferential bank has an average slope angle of from about 5 degrees to about 85 degrees or from about 95 degrees to about 175 degrees and the inside wall of the raised circumferential bank has an average slope angle of from about 5 degrees to about 85 degrees or from about 95 degrees to about 175 degrees.

8. The absorbent article of claim 7, wherein the raised circumferential bank is formed by a single resilient material.

9. The absorbent article of claim 7, wherein the body facing surface has a second concave portion, and wherein the raised circumferential bank is disposed within the second concave portion.

10. The absorbent article of claim 7, wherein the resilient material is formed by a moldable material.

11. The absorbent article of claim 10, wherein the moldable material is selected from the group consisting of a polymeric foam material, a fibrous material, an elastic material, a formed film material, an absorbent gelling material, and a mixture thereof.

12. The absorbent article of claim 7, wherein the shape of the body facing surface of the absorbent article further forms a raised saddle bank in the rear region.

13. The absorbent article of claim 1 or 7, wherein the absorbent article is a sanitary napkin, pantiliner, or an incontinence pad.

* * * * *

UNITED STATES PATENT AND TRADEMARK OFFICE
CERTIFICATE OF CORRECTION

PATENT NO. : 7,037,298 B2  Page 1 of 1
APPLICATION NO. : 10/302601
DATED : May 2, 2006
INVENTOR(S) : Kenji Ohshima et al.

It is certified that error appears in the above-identified patent and that said Letters Patent is hereby corrected as shown below:

Column 6, line 23, "50 g/cm" should read --50 g/cm$^2$ --.

Signed and Sealed this

Fourth Day of July, 2006

JON W. DUDAS
*Director of the United States Patent and Trademark Office*